(12) United States Patent
Martinez et al.

(10) Patent No.: US 6,730,805 B2
(45) Date of Patent: May 4, 2004

(54) SYNTHESIS OF 2H- AND 13C-SUBSTITUTED COMPOUNDS

(75) Inventors: Rodolfo A. Martinez, Santa Fe, NM (US); Marc A. Alvarez, Santa Fe, NM (US); Louis A. Silks, III, Los Alamos, NM (US); Clifford J. Unkefer, Los Alamos, NM (US)

(73) Assignee: The Regents of the University of California, Los Alamos, NM (US)

( * ) Notice: Subject to any disclaimer, the term of this patent is extended or adjusted under 35 U.S.C. 154(b) by 0 days.

(21) Appl. No.: 10/405,683

(22) Filed: Apr. 1, 2003

(65) Prior Publication Data

US 2003/0204108 A1 Oct. 30, 2003

Related U.S. Application Data

(62) Division of application No. 10/074,669, filed on Feb. 13, 2002, now Pat. No. 6,541,671.

(51) Int. Cl.[7] ............................................. C07C 69/02
(52) U.S. Cl. ....................... 560/231; 560/129; 424/1.65; 424/1.81
(58) Field of Search ............................... 424/1.65, 1.81; 560/129, 231, 254

(56) References Cited

U.S. PATENT DOCUMENTS

| | | |
|---|---|---|
| 5,527,937 A | 6/1996 | Standke et al. |
| 5,536,860 A | 7/1996 | Monkiewicz et al. |
| 5,629,400 A | 5/1997 | Standke et al. |
| 5,646,325 A | 7/1997 | Monkiewicz et al. |
| 5,679,147 A | 10/1997 | Standke et al. |
| 5,808,125 A | 9/1998 | Standke et al. |
| 5,849,942 A | 12/1998 | Standke et al. |
| 5,863,509 A | 1/1999 | Standke et al. |
| 5,885,341 A | 3/1999 | Standke et al. |
| 5,932,757 A | 8/1999 | Standke et al. |
| 6,084,116 A | 7/2000 | Horn et al. |
| 6,177,582 B1 | 1/2001 | Jenkner et al. |
| 6,177,584 B1 | 1/2001 | Loewenberg et al. |
| 6,228,936 B1 | 5/2001 | Standke et al. |
| 6,239,194 B1 | 5/2001 | Standke et al. |
| 6,251,989 B1 | 6/2001 | Edelmann et al. |
| 6,255,516 B1 | 7/2001 | Jenkner et al. |
| 6,288,256 B1 | 9/2001 | Standke et al. |
| 6,361,871 B1 | 3/2002 | Jenkner et al. |
| 6,395,858 B1 | 5/2002 | Mack et al. |
| 6,403,228 B1 | 6/2002 | Mack et al. |
| 6,491,838 B1 | 12/2002 | Standke et al. |
| 6,500,883 B1 | 12/2002 | Mack et al. |
| 6,528,585 B1 | 3/2003 | Standke et al. |
| 6,534,667 B1 | 3/2003 | Standke et al. |

OTHER PUBLICATIONS

CA:89:128836 abs of Phosphorus and Sulfur and the Related Elements by Furukawa et al 3(3) pp 277–280 1977.*
CA:85:77804 abs of Journal of Organic Chemistry by Harris et al 41 (16) pp 2770–2 1976.*
CA:100:209138 abs of Tetrahedron Letters by Ungen, D. 25(5) pp 541–2 1984.*
CA:126:263907 abs of Journal of Chinese Chem Soc (Taipei) by Let , Ren Shen 44(1) pp77–80.*
CA:122:290154 abs of Journal of Chem Soc Chem Comm. by Chowdhury et al 17 pp 1993–4 1994.*
CA:108:74901 abs of Chemistry Letters by Koizumi et al (6) pp 1095–6 1987.*
CA:105:171738 abs of Australian Journal of Chem by Beckwith et al 39 (1) pp 77–87 1986.*

* cited by examiner

*Primary Examiner*—Jean F. Vollano
(74) *Attorney, Agent, or Firm*—Bruce H. Cottrell

(57) ABSTRACT

The present invention is directed to labeled compounds, [2-$^{13}$C]dithane wherein the $^{13}$C atom is directly bonded to one or two deuterium atoms. The present invention is also directed to processes of preparing [2-$^{13}$C]dithane wherein the $^{13}$C atom is directly bonded to one or two deuterium atoms. The present invention is also directed to labeled compounds, e.g., [$^{2}$H$_{1-2}$, $^{13}$C]methanol (arylthio)-, acetates wherein the $^{13}$C atom is directly bonded to exactly one or two deuterium atoms.

5 Claims, No Drawings

SYNTHESIS OF 2H- AND 13C-SUBSTITUTED COMPOUNDS

This application is a divisional of Ser. No. 10/074,669 filed, Feb. 13, 2002, now U.S. Pat. No. 6,541,671 by Martinez et al.

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates to labeled compounds and more particularly to compounds labeled with carbon-13 and hydrogen-2.

BACKGROUND OF THE INVENTION

Stable isotope labeled amino acids and nucleotides are required for structural and mechanistic studies of proteins and oligonucleotides. In addition, isotopically labeled biologically active compounds are required for many phases of drug discovery and development including elucidation of biosynthetic pathways, pharmacokinetics, and drug metabolism. For many applications, site-specific $^{13}$C or combined $^{13}$C and $^2$H labeling are required. While a number of stable isotope labeled compounds are available from companies such as Sigma-Aldrich Chemicals, a need remains for other labeled synthetic precursors.

Dithane has been used in a wide number of reactions to make a large number of such biomolecules and other important synthetic precursors. For example, dithane can be used as a nucleophilic synthon. While dithane could provide a chemically stable and non-volatile carrier for the valuable $^{13}$C and $^2$H labels, the preparation of isotopically labeled dithane has not been previously accomplished. Thus, availability of $^2$H- and $^{13}$C-substituted dithanes would allow researchers to take advantage of the wealth of chemistry that has been done using unlabeled methyl phenyl sulfide.

As carbon-13 is separated from its lighter isotope by cyrogenic distillation of carbon monoxide (CO), all labeled carbons are derived ultimately from CO. The highly efficient conversion of CO to useful chemical precursors is perhaps the most unique aspect of stable isotope labeling technology. Any inefficiencies in the early synthetic steps add greatly to the overall expense of isotope labeling. Thus, considerable efforts have been directed to the development of methods for the preparation of useful synthetic precursors or synthons. This effort has given rise to efficient large-scale methods for the synthesis of methane, methanol, methyl iodide, sodium formate, potassium cyanide and carbon dioxide. These methods are the foundation of all labeling chemistry. The most useful of the electrophilic one-carbon precursors, methyl iodide and carbon dioxide, are difficult to store and use efficiently due to their high volatility.

As spectroscopic instrumentation and techniques continue to improve, there is a drive to study ever more complicated bio-systems. This has lead to demands for more complex labeling patterns in biomolecules. In the past, the simple introduction of a labeled atom site-specifically without stereospecificity was the major thrust for stable isotope labeling and the first generation of labeled synthons served this effort well. Increasingly, in today's labeling climate, in addition to site-specific labeling, the requirement for stereospecificity has been added. This includes both the ability to stereospecific label chiral compounds as well as the ability to differentiate between prochiral centers with deuterium or carbon. Additional synthons as starting materials will address those growing demands.

It is an object of the present invention to provide labeled compounds.

SUMMARY OF THE INVENTION

In accordance with the purposes of the present invention, as embodied and broadly described herein, the present invention provides the labeled compound, [2-$^{13}$C]dithane wherein the $^{13}$C is directly bonded to exactly one or two deuterium atoms.

The present invention further provides a process of preparing compounds such as [2, 2-$^2$H$_2$, 2-$^{13}$C]dithane by reacting [$^2$H$_3$, $^{13}$C]methyl phenyl sulfoxide with sodium acetate to form an intermediate product; and, reacting said intermediate product with HS—(CH$_2$)$_3$—SH to form [2, 2-$^2$H$_2$, 2-$^{13}$C]dithane.

The present invention still further provides labeled compounds, of the structure Ar—S—C*D$_{2-x}$H$_x$—O—R where Ar is an aryl group, C* is a $^{13}$C labeled carbon atom, D is a $^2$H, x is 0 or 1, and R is selected from a C$_1$–C$_5$ lower alkyl group or an acyl group including a C$_1$–C$_5$ lower alkyl group substituent, i.e., the acyl group is (—C(O)R$^1$) where R$^1$ is a C$_1$–C$_5$ lower alkyl. In a preferred embodiment, R is an acyl group wherein R$^1$ is methyl such that the labeled compounds are [$^2$H$_{1-2}$, $^{13}$C]methanol(arylthio)-, acetates wherein said $^{13}$C atom is directly bonded to exactly one or two deuterium atoms.

DETAILED DESCRIPTION

Dithane is a useful organic reagent that allows for the construction of many useful biochemicals and materials. Isotopically labeled dithane can be used to introduce a carbon-13 and a hydrogen-2 or deuterium label [$^2$H] into such biochemicals and materials.

As used herein, the term "aryl" means a monovalent monocyclic or bicyclic aromatic hydrocarbon radical of 6 to 10 ring atoms, and optionally substituted independently with one, two, three, four or five substituents selected from alkyl, haloalkyl, cycloalkyl, halo, nitro, cyano, —OR (where R is hydrogen, alkyl, haloalkyl, cycloalkyl, optionally substituted phenyl), acyl, and —COOR (where R is hydrogen or alkyl). More specifically the term aryl includes, but is not limited to, phenyl, 1-naphthyl, 2-naphthyl, and derivatives thereof.

As used herein, the term "acyl" means a (—C(O)R$^1$ group) aryl or aliphatic acyl groups where R$^1$ is, e.g., a C$_{1-5}$ lower alkyl. Examples of acyl include straight chain or branched alkanoyls such as formyl; acetyl, propanoyl, butanoyl, 2-methylpropanoyl, and pentanoyl. Preferably the acyl is acetyl.

In one embodiment of the invention, [2, 2-$^2$H$_2$, 2-$^{13}$C] dithane can be made from [$^2$H$_3$, $^{13}$C]methyl phenyl sulfoxide in process as shown below. The [2, 2-$^2$H$_2$, 2-$^{13}$C]dithane can be used as a non-volatile carrier of the desired carbon and hydrogen labels.

$^{13}$CD$_3$S(O)-aryl $\xrightarrow{\begin{array}{c}\text{1. sodium acetate, acetic anhydride}\\\text{2. HS—(CH}_2\text{)}_3\text{—SH, CH}_2\text{Cl}_2\end{array}}$

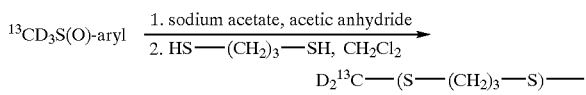

Availability of the [2, 2-$^2$H$_2$, 2-$^{13}$C]dithane will allow researchers to take advantage of the wealth of chemistry that has been done using unlabeled dithane.

The present invention provides efficient large scale processes for the preparation of [2, 2-$^2$H$_2$, 2-$^{13}$C]dithane from

[$^2H_3$, $^{13}C$]methyl phenyl sulfoxide. Dithane provides a chemically stable and non-volatile carrier for the valuable $^{13}C$ and $^2H$ labels.

In the process of the present invention, [2, 2-$^2H_2$,2-$^{13}C$]dithane can be prepared in a high yield (>95%) process by first reacting [$^2H_3$, $^{13}C$]methyl phenyl sulfoxide with, e.g., a sodium acylate, preferably sodium acetate, in acetic anhydride to form an intermediate and reacting the intermediate with HS—(CH$_2$)$_3$—SH in methylene chloride to produce the dithane. Optionally, the dithane may be prepared with only a single deuterium atom on the $^{13}C$ labeled atom by altering the deuterium substitution on the [$^{13}C$]methyl phenyl sulfoxide.

The present invention is more particularly described in the following examples which are intended as illustrative only, since numerous modifications and variations will be apparent to those skilled in the art.

EXAMPLE 1

[$^{13}C$]Methyl phenyl sulfide was prepared as follows. A one-liter, two-neck flask was fitted with an argon inlet adapter and an air-cooled condenser. This flask was charged with 46.2 gram (g) (1.40 mole) [$^{13}C$]methanol (99% $^{13}C$) and 726 milliliter (ml) (4.20 mole, 3.00 equivalents (eq)) hydroiodic acid (HI) (47% by weight solution in water). The air-cooled condenser was fitted with an outlet adapter, which in turn was attached (via a short piece of Tygon® tubing) to a long solvent trap immersed in an ice-water bath. This ice-cooled solvent trap was connected to an inlet adapter on a two-liter, two-neck flask containing a vigorously stirring biphasic mixture of 169.7 g (1.54 mole, 1.10 eq) thiophenol and 140 g (3.50 mole, 2.50 eq) of sodium hydroxide (NaOH) in a mixture of 400 ml benzene and 300 ml water. The second neck of this flask was fitted with an isopropanol/dry ice-cooled condenser with an argon outlet. The [$^{13}C$]methanol/HI solution was then heated at 85° C. for 2 hours, and then heating was discontinued. Again, any [$^{13}C$]methyl iodide, which had collected in the ice-cooled trap was transferred to the sodium-thiophenoxide mixture, and this mixture was allowed to stir overnight. The mixture was then transferred to a separatory funnel containing 400 ml of ethyl ether (Et$_2$O), the organic phase was washed with three 100 ml portions of water, and then dried over sodium sulfate (Na$_2$SO$_4$). Removal of the solvents under reduced pressure gave 168 g (95.6% theoretical yield) of [$^{13}C$]methyl phenyl sulfide as a clear, colorless oil: $^1$H NMR (500 MHz, CDCl$_3$) ∂2.33–2.61 (d,3H,J=139.6 Hz), 7.11–7.26(m, 5H); $^{13}C$ NMR (125 MHz, CDCl$_3$) ∂ 138.4, 128.8, 126.7, 125.0, 15.9.

EXAMPLE 2

[$^2H_3$, $^{13}C$]Methyl phenyl sulfide was prepared as follows from [$^2H_4$, $^{13}C$]methanol using the procedure of Example 1. From 36.6 g (0.987 mole) of [$^2H_4$, $^{13}C$]methyl alcohol, 540 ml (2.96 mole, 3.00 e q) HI (47% aqueous solution), 120 g (1.09 mole, 1.10 eq) thiophenol, and 98.7 g (2.47 mole, 2.50 eq) NaOH was obtained 125 g (98.6% theoretical yield) [$^2H_3$, $^{13}C$]-methyl phenyl sulfide as a clear, slightly yellow oil: $^1$H NMR (300 MHz, CDCl$_3$) ∂ 7.10–7.26 (m, 5H); $^{13}C$(75 MHz, CDCl$_3$) ∂ 138.4, 128.8, 126.7, 125.0, {16.0, 15.7, 15.4, 15.1, 14.9, 14.6, 14.3 (septet, J=21.3 Hz)}.

EXAMPLE 3

[$^2H_3$, $^{13}C$]Methyl phenyl sulfoxide was prepared as follows. A 30% aqueous solution of hydrogen peroxide (19.53 g; 0.17 moles, 1.2 eq.) was added to a ethanol solution (184 ml) of [$^2H_3$, $^{13}C$]methyl phenyl sulfide (18.4 g, 0.14 moles). The reaction was stirred at room temperature for 3 days. After this period the reaction was complete and ethyl acetate (300 mL) was added to the reaction. The reaction was transferred to a separatory funnel and an equal volume of water was added. The organic layer was recovered and the aqueous layer was extracted twice more with ethyl acetate (2×300 mL). The combined organic phases are dried with Na$_2$SO$_4$ then filtered and solvents evaporated. Remaining solvent was removed from the solid under vacuum using a liquid nitrogen cooled trap. [$^2H_3$, $^{13}C$]Methyl phenyl sulfoxide (19.45 g; 94%) was obtained as a colorless oil, pure by NMR (>98%), which could be used in subsequent reactions without further purification. $^1$H [CDCl$_3$, 300 MHz] 7.56–7.95 (m, 5H), $^{13}C$ [CDCl$_3$, 75 MHz] 43.07 (heptet, J=21 Hz) 123.38, 129.26, 130.94, 145.44.

EXAMPLE 4

[$^2H_2$, $^{13}C$]Methanol (phenylthio)-, acetate was prepared as follows. [$^2H_3$, $^{13}C$]Methyl phenyl sulfoxide (10.0, 0.07 moles) was dissolved in acetic anhydride (50 mL). Solid sodium acetate (NaOAc) (11.39 g, 0.14 moles) was added to the solution and the resulting mixture was heated at reflux for 24 hours. The reaction was cooled and added to a mixture of ethyl acetate (400 mL) and saturated sodium bicarbonate (200 mL). The biphasic mixture was stirred for 2 hours and then separated in a separatory funnel. The aqueous layer was washed with additional ethyl acetate (2×200 mL). The combined organic phases are dried with Na$_2$SO$_4$ then filtered and solvents evaporated. Remaining solvent was removed from the solid under vacuum using a liquid nitrogen cooled trap. [$^2H_2$, $^{13}C$]Methanol (phenylthio)-, acetate (12.84 g; 90%) was obtained as a colorless oil, pure by NMR (>98%), which could be used in subsequent reactions without further purification. $^1$H [CDCl$_3$, 300 MHz] 2.11 (s, 3H) 7.29–7.50 (m, 5H), $^{13}C$ [CDCl$_3$, 75 MHz] 20.84, 67.6 (pentet, J=21 Hz) 127.11, 128.92, 130.03, 134.47, 170.03.

EXAMPLE 5

[2, 2-$^2H_2$, 2-$^{13}C$]Dithane was prepared as follows. [$^2H_2$, $^{13}C$]Methanol (phenylthio)-, acetate (2 g, 0.010 moles) was dissolved in toluene (20 mL). Propane dithiol (1.40 g, 0.013 moles) was added via a syringe to the toluene solution. To this solution an equal weight of Amberlyst® ion exchange resin (2 g) was added as a solid. The reaction mixture was refluxed for 3 days after which the reaction was complete as monitored by NMR. The reaction was filtered and the solid Amberlyst® ion exchange resin was washed with toluene (2×50 mL). The combined organic phase was washed with brine (3×50 mL) dried over Na$_2$SO$_4$ then filtered and evaporated. The mixture, ([2, 2-$^2H_2$, 2-$^{13}C$]dithane and propane dithiol), was purified by column chromatography (silica gel, 10% ethyl acetate, hexane). [2, 2-$^2H_2$, 2-$^{13}C$]Dithane (1.30 g, 99%) was obtained as a colorless oil, pure by NMR (>98%). $^1$H [CDCl$_3$, 300 MHz] 2.11 (m, 2H) 2.09–2.05 (m, 4H), $^{13}C$ [CDCl$_3$, 75 MHz] 26.52, 29.52 (pentet, J=21 Hz) 31.36.

Although the present invention has been described with reference to specific details, it is not intended that such details should be regarded as limitations upon the scope of the invention, except as and to the extent that they are included in the accompanying claims.

What is claimed is:

1. A labeled compound of the structure Ar—S—C*$D_{2-x}$$H_x$—O—R where Ar is an aryl group, 0* is a $^{13}C$ labeled carbon atom, D is a $^2H$, x is 0 or 1, and R is acyl groups including a $C_1$–$C_5$ lower alkyl group substituent.

2. The compound of claim 1 wherein said labeled compound is a deuterated $^{13}C$ arylthio methanol acetate of formula (A) or formula (B) wherein formula (A) is ArS—$^{13}CD_2$—OC(O)$CH_3$ and formula (B) is ArS—$^{13}CD(H)$—OC(O)$CH_3$.

3. The compound of claim 2, wherein said labeled compound is a deuterated $^{13}C$ phenylthio methanol acetate of formula (A) or formula (B) wherein formula (A) is PhS—$^{13}CD_2$—OC(O)$CH_3$ and formula (B) is PhS—$^{13}CD(H)$—OC(O)$CH_3$.

4. The compound of claim 1 wherein said aryl is selected from the group consisting of phenyl, 1-naphthyl, 2-naphthyl.

5. The compound of claim 1 wherein said aryl is phenyl.

* * * * *